United States Patent [19]

Miyazaki et al.

[11] Patent Number: 5,689,114
[45] Date of Patent: Nov. 18, 1997

[54] GAS ANALYZING APPARATUS

[75] Inventors: Tadashi Miyazaki; Kazuhiro Kawasaki, both of Hachioji, Japan

[73] Assignee: Jasco Corporation, Hachioji, Japan

[21] Appl. No.: 632,881

[22] Filed: Apr. 16, 1996

[30] Foreign Application Priority Data

Apr. 28, 1995 [JP] Japan .................................. 7-129042

[51] Int. Cl.⁶ .................................................. G01N 21/61
[52] U.S. Cl. ............................................ 250/343; 250/345
[58] Field of Search ............................. 250/343, 345, 250/339.13

[56] References Cited

U.S. PATENT DOCUMENTS

| | | | |
|---|---|---|---|
| 3,384,749 | 5/1968 | Golay . | |
| 3,916,195 | 10/1975 | Burch et al. | 250/345 |
| 3,968,367 | 7/1976 | Berg | 250/343 |
| 4,154,089 | 5/1979 | Carlon | 250/343 |
| 4,228,352 | 10/1980 | Adrian | 250/343 |
| 4,684,805 | 8/1987 | Lee et al. | 250/343 |
| 4,891,518 | 1/1990 | Day | 250/343 |
| 5,146,294 | 9/1992 | Grisar et al. | 250/345 |

FOREIGN PATENT DOCUMENTS

| | | |
|---|---|---|
| 0 584 897 A1 | 7/1993 | European Pat. Off. . |
| 0 634 644 A1 | 6/1994 | European Pat. Off. . |
| 8902312 U | 5/1990 | Germany . |
| 53-9889 | 8/1978 | Japan . |

*Primary Examiner*—Carolyn E. Fields
*Attorney, Agent, or Firm*—Ronald R. Snider

[57] ABSTRACT

A gas analyzing apparatus comprises a light source (34) emitting an infrared luminous flux; a sample cell (38) which is arranged such that a sample gas is introduced therein and the infrared luminous flux emitted from the light source (34) is transmitted therethrough; and detection means (10a, 10b) which contain absorbers and are arranged such that the infrared luminous flux transmitted through the sample cell (38) passes through the absorbers and an increase in pressure according to the temperature within each of their absorber containers raised upon absorption of the infrared luminous flux by each absorber is optically detected so as to measure, based on the increases in pressure, concentrations of ingredients to be measured in the sample gas, wherein, as the absorbers contained in the detection means (10a, 10b), gases having ingredients identical to the ingredients to be measured are used, respectively.

17 Claims, 6 Drawing Sheets

GAS ANALYZING APPARATUS

RERATED APPLICATIONS

This application claims the priority of Japanese Patent Application No.7-129042 filed on Apr. 28, 1995, which is incorporated herein by reference.

FIELD OF THE INVENTION

The present invention relates to a gas analyzing apparatus and, in particular, to an improvement in its detection means.

BACKGROUND OF THE INVENTION

In general, a molecular composed of different kinds of atoms (e.g., carbon monoxide or carbon dioxide) has a characteristic to absorb an infrared ray having an inherently distinctive wavelength. A method utilizing this technique to selectively measure the concentration of a gas is called nondispersive infrared absorption method and widely used as a process continuous concentration analyzer.

The nondispersive infrared analyzers are roughly divided into thermal type and quantum type according to their principles for measurement. The thermal type can be divided into pneumatic type, pyroelectric type, resistor type, and thermocouple type. The pneumatic type can be further divided into condenser microphone type and Golay cell type.

As a gas analyzing apparatus, the condenser microphone type has been universally used. This is because it has a relatively simple configuration and advantageous effects such as a high steadiness. Also, it is advantageous, for example, in that a high selectivity can be obtained with respect to various measurement ingredients when a detector containing a measurement ingredient is selected.

However, while the condenser microphone type gas analyzing apparatus has the above-mentioned advantageous effects, its sensitivity is not so excellent.

SUMMARY OF THE INVENTION

In view of the foregoing problem of the prior art, the object of the present invention is to provide a gas analyzing apparatus which is also excellent in sensitivity.

In order to attain the above-mentioned object, the gas analyzing apparatus in accordance with the present invention comprises a light source emitting an infrared luminous flux; a sample cell which is arranged such that a sample gas is introduced therein and the infrared luminous flux emitted from the light source is transmitted therethrough; and a detection means which contains an absorber and is arranged such that the infrared luminous flux transmitted through the sample cell passes through the absorber and an increase in pressure according to the temperature within its absorber container raised upon absorption of the infrared luminous flux by the absorber is optically detected so as to measure, based on the increase in pressure, the concentration of an ingredient to be measured in the sample gas, wherein, as the absorber contained in the detection means, a gas having an ingredient identical to the ingredient to be measured is used.

When the gas analyzing apparatus measures concentrations of a plurality of ingredients in the sample gas, it preferably has at least two detection means containing gases having ingredients identical to the plurality of measurement ingredients, respectively.

Preferably, the gas analyzing apparatus has at least one detection means containing a reference ingredient gas and the other detection means containing a gas having an ingredient identical to the ingredient to be measured and further comprises a comparator means which compares the concentration value obtained from the detection means containing the gas having an ingredient identical to the ingredient to be measured with the concentration value obtained from the detection means containing a reference ingredient gas.

Preferably, the gas analyzing apparatus has a common power source for detection light sources for the plurality of detection means.

Preferably, the gas analyzing apparatus has a common light source for emitting the infrared luminous flux.

Preferably, in the gas analyzing apparatus, the sample cell comprises at least two cell portions and the cell portions are formed with a long optical path length when the ingredient to be measured has a low concentration, whereas the cell portions are formed with a short optical path length when the ingredient to be measured has a high concentration.

Preferably, in the gas analyzing apparatus, on a path between the sample cell and detection means through which the infrared luminous flux passes, a gas filter containing a gas having an ingredient identical to the ingredient contained in another detection means is disposed.

Preferably, in the gas analyzing apparatus, on a path between the sample cell and detection means through which the infrared luminous flux passes, an optical filter which cuts off, from the infrared luminous flux transmitted through the sample cell, a wavelength inherent in the gas contained in another detection means is disposed.

Preferably, a condenser lens is used in an exit window of the sample cell

Preferably, in the gas analyzing apparatus, the sample cell comprises a light pipe whose inside is optically polished.

Preferably, in the gas analyzing apparatus, the sample cell is bent at a plurality of portions thereof and a reflective mirror is disposed at each bent portion of the sample cell.

Preferably, the gas analyzing apparatus has a thermostat means which can constantly maintain the temperature of the sample gas within the sample cell.

Preferably, the gas analyzing apparatus has a means which can homogenize the mixed state of the sample gas within the sample cell.

Further, preferably, the gas analyzing apparatus has a single sample cell into which the sample gas is introduced and at least one reflective mirror which is disposed on a path between the light source emitting the infrared luminous flux and the sample cell, through which the infrared luminous flux passes, such that one part of the luminous flux from the light source is transmitted through the sample cell in its longitudinal direction while the other part is transmitted therethrough in its lateral direction so as to enter their corresponding detection means.

Thus, in the gas analyzing apparatus in accordance with the present invention, due to the foregoing means, the infrared luminous flux from the light source enters the detection means with its quantity of light changed according to the concentration of the ingredient to be measured in the sample gas which has been introduced into the sample cell.

Here, the detection means contains a gas having an ingredient identical to the ingredient to be measured. The gas contained in this detection means absorbs, from the infrared luminous flux transmitted through the sample cell, only the infrared luminous flux having a wavelength identical to the wavelength inherent in the ingredient to be measured. When the gas contained in the detection means absorbs the infrared luminous flux having this inherent wavelength, in response to thus absorbed quantity of light, the temperature within the gas container rises, thereby increasing the pressure therewithin.

Therefore, the measurement means can detect the increase in pressure within the gas container containing a gas having an ingredient identical to the ingredient to be measured and, based on the increase in pressure, measure the concentration of the ingredient to be measured in the sample gas with a high sensitivity.

Further, when the detection means containing a gas having an ingredient identical to the ingredient to be measured is selected, a high selectivity can be obtained with respect to various kinds of measurement ingredients.

Also, when a plurality of ingredients in a sample gas are measured, at least two detection means containing gases having ingredients identical to the plurality of ingredients, respectively, can be disposed so as to simultaneously measure the concentrations of the plurality of ingredients in the sample gas.

When the gas analyzing apparatus has at least one detection means containing a reference ingredient gas and the other detection means containing a gas having an ingredient identical to the ingredient to be measured and further comprises a comparator means which compares the concentration value obtained from the detection means containing the gas having an ingredient identical to the ingredient to be measured with the concentration value obtained from the detection means containing a reference ingredient gas, by performing this comparison, stability in measurement results can be improved.

When the gas analyzing apparatus has a common power source for detection light sources for the plurality of detection means, error values in the detection means resulting from power source noise can coincide with each other. Accordingly, such errors in measurement can be offset against each other, whereby the concentration of the ingredient to be measured in the sample gas can be measured correctly.

Also, when the gas analyzing apparatus has a common light source for emitting an infrared luminous flux, error values resulting from fluctuation in luminance of the light source can coincide with each other. Accordingly, such errors in measurement can be offset against each other, whereby the concentration of the ingredient to be measured in the sample gas can be measured correctly.

When the sample cell comprises at least two cell portions and the cell portions are formed with a long optical path length when the ingredient to be measured has a low concentration, whereas the cell portions are formed with a short optical path length when the ingredient to be measured has a high concentration, the output values of the plurality of detection means have an improved balance, whereby the concentration of various ingredients in the sample gas can be measured with a high sensitivity.

In cases where, on a path between the sample cell and detection means through which the infrared luminous flux passes, a gas filter containing a gas having an ingredient identical to the ingredient contained in another detection means is disposed, from the infrared luminous flux transmitted through the sample cell, only the infrared luminous flux having a wavelength substantially identical to the wavelength inherent in the gas contained in this detection means can be transmitted therethrough. Accordingly, even when an ingredient other than the ingredient to be measured is mingled into the gas container of the detection means, the error in measurement resulting from the absorption of the infrared luminous flux by the ingredient other than the ingredient to be measured is prevented from occurring, whereby the concentration of only the ingredient to be measured can be correctly measured.

Also, in cases where, on a path between the sample cell and detection means through which the infrared luminous flux passes, an optical filter which cuts off, from the infrared luminous flux passes, an optical filter which cuts off, from the gas contained in another detection means is disposed, even when an ingredient other than the ingredient to be measured is mingled into the gas container of the detection means, the error in measurement resulting from the absorption of the infrared luminous flux by the ingredient other than the ingredient to be measured is prevented from occurring, whereby the concentration of only the ingredient to be measured can be correctly measured.

When a condenser lens is used in an exit window of the sample cell, the infrared luminous flux transmitted through the sample cell can be efficiently converged onto the detection means. Accordingly, the detection means can correctly measure the concentration of the ingredient to be measured in the sample cell. Also, cost can be reduced as compared in the case where the exit window of the sample cell and the condenser lens are disposed separately from each other.

When the sample cell comprises a light pipe whose inside is optically polished, the infrared luminous flux from the light source can efficiently be transmitted through the sample cell. Accordingly, the detection means can correctly measure the concentration of the ingredient to be measured in the sample cell.

When the sample cell is bent at a plurality of portions thereof and a reflective mirror is disposed at each bent portion of the sample cell, the sample cell can have a smaller size without shortening its whole optical path length, thereby reducing the size of the apparatus.

When the gas analyzing apparatus has a thermostat means which can constantly maintain the temperature of the sample gas within the sample cell, the error in measurement due to changes in the outside air temperature and the temperature within the chamber can be prevented from occurring, whereby correct and stable results in measurement can be obtained even when the apparatus is used for a long period of time.

When the gas analyzing apparatus has a means which can homogenize the mixed state of the sample gas within the sample cell, the sample gas is prevented from generating a convection due to changes in the infrared luminous flux from the light source and the outside air temperature and the ingredients are prevented from being unevenly distributed due to their difference in specific gravity, whereby the concentrations of the ingredients to be measured in the sample cell can be correctly measured.

Further, when the gas analyzing apparatus has a single sample cell into which a sample gas is introduced and at least one reflective mirror which is disposed on a path between the light source emitting the infrared luminous flux and the sample cell, through which the infrared luminous flux passes, such that one part of the luminous flux from the light source is transmitted through the sample cell in its longitudinal direction while the other part is transmitted therethrough in its lateral direction so as to enter their corresponding detection means, the sample gas can be rapidly introduced into the sample cell and rapidly stabilized in the sample cell.

DETAILED DESCRIPTION OF THE PREFERRED EMBODIMENTS

In the following, preferred embodiments of the present invention will be explained with reference to drawings. Here, each drawing merely shows a basic configuration of the gas analyzing apparatus in these embodiments. Such a basic configuration may be modified in terms of its forms or additional components within the scope of the technological idea of the present invention.

Figure 1:
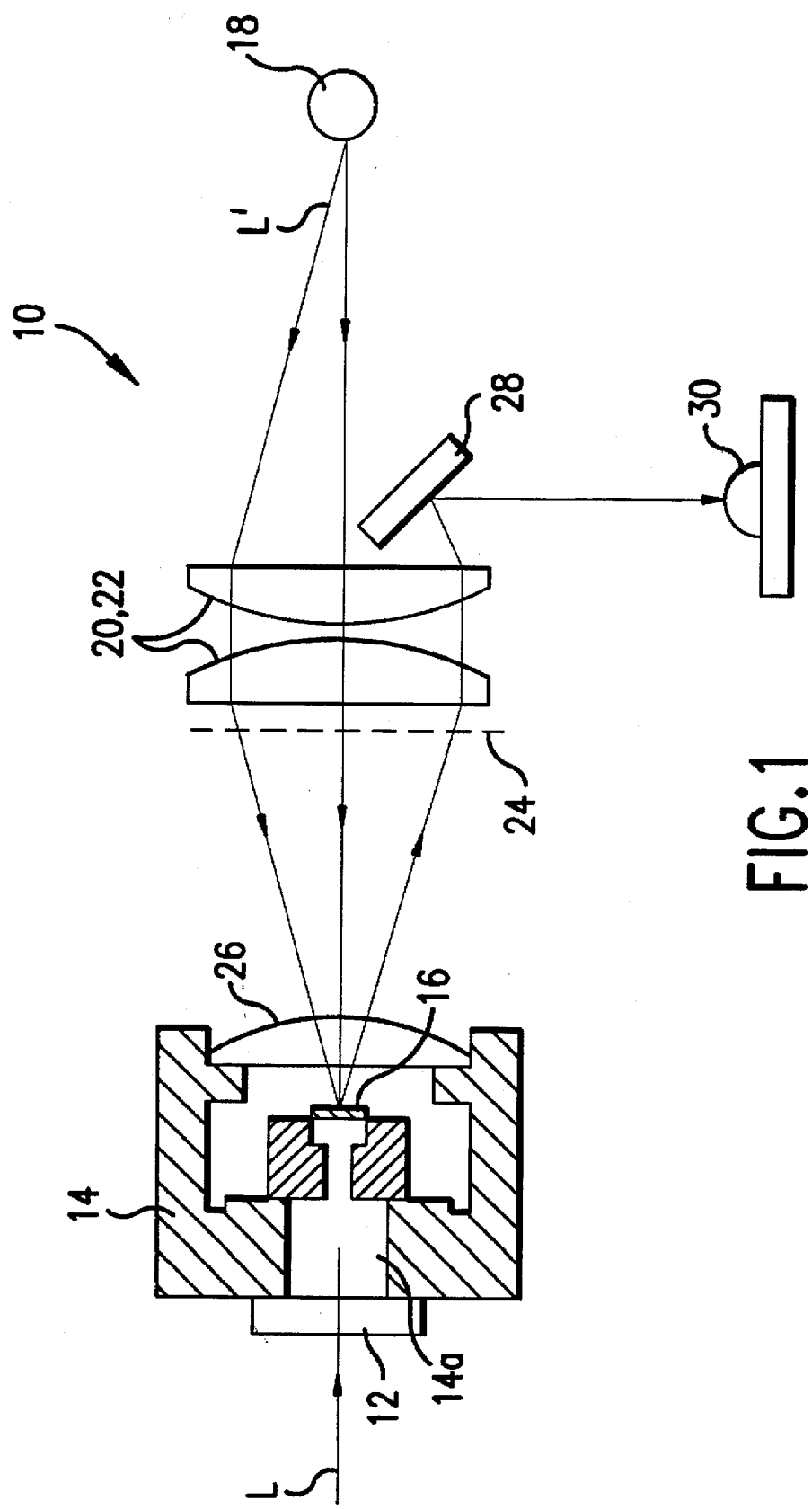
FIG. 1 is an explanatory view showing a configuration of a detection means in a gas analyzing apparatus in accordance with one embodiment of the present invention.

FIG. 1 is a schematic view showing the configuration of a detection means 10 which is a characteristic feature of the gas analyzing apparatus in accordance with an embodiment of the present invention.

Also, in this embodiment, for example, assuming that a sample gas is an exhalation, explanations will be provided for a case where $^{12}CO_2$ and $^{13}CO_2$ concentrations in the exhalation are measured.

As depicted, an infrared luminous flux transmitted through the sample gas passes through an inlet window portion 12 of the detection means 10 so as to enter a gas container 14a from one end of a chamber 14.

Here, the gas container 14a of the chamber 14a contains, for example, only $^{13}CO_2$ gas. This $^{13}CO_2$ gas absorbs, from the infrared luminous flux L which has entered the gas container 14a, only the infrared luminous flux having a wavelength identical to the wavelength inherent in the $^{13}CO_2$ gas. Then, when the $^{13}CO_2$ gas absorbs this infrared luminous flux and thereby the temperature increases, the pressure within the gas container 14a increases.

Also, the gas container 14a of the chamber 14 has a variable mirror 16 made of a thin film such that the surface thereof can bend according to a change in the air pressure. Onto the variable mirror 16, by way of a pair of condenser lenses 20 and 22 and a grating 24, light L' emitted from a detection light source 18 of the detection means 10 is converged by a lens 26 disposed at another end of the chamber 14.

The light L' from the detection light source 18 converged onto the variable mirror 16 is reflected thereby and, again by way of the lens 26, forms an image of the grating, through which the light L' has previously passed, upon the grating 24.

Here, when the variable mirror is bent due to the increase in pressure within the gas container 14a, the grating image and the grating 24 deviate from each other and the light L' slightly leaks therefrom due to this deviation. Thus leaked light L' passes through the condenser lenses 20 and 22 and then is projected by a reflective mirror 28 onto a detecting portion 30.

Since the light quantity of the light L' from the detection light source 18 projected onto the detecting portion 30 is proportional to the light quantity of the infrared luminous flux L which has entered the detection means 10 and then been absorbed by the $^{13}CO_2$ gas within the gas container 14a, from the infrared luminous flux L entering the detection means 10, only the intensity of the infrared luminous flux having a wavelength identical to the wavelength inherent in the $^{13}CO_2$ gas can be measured.

Figure 2:
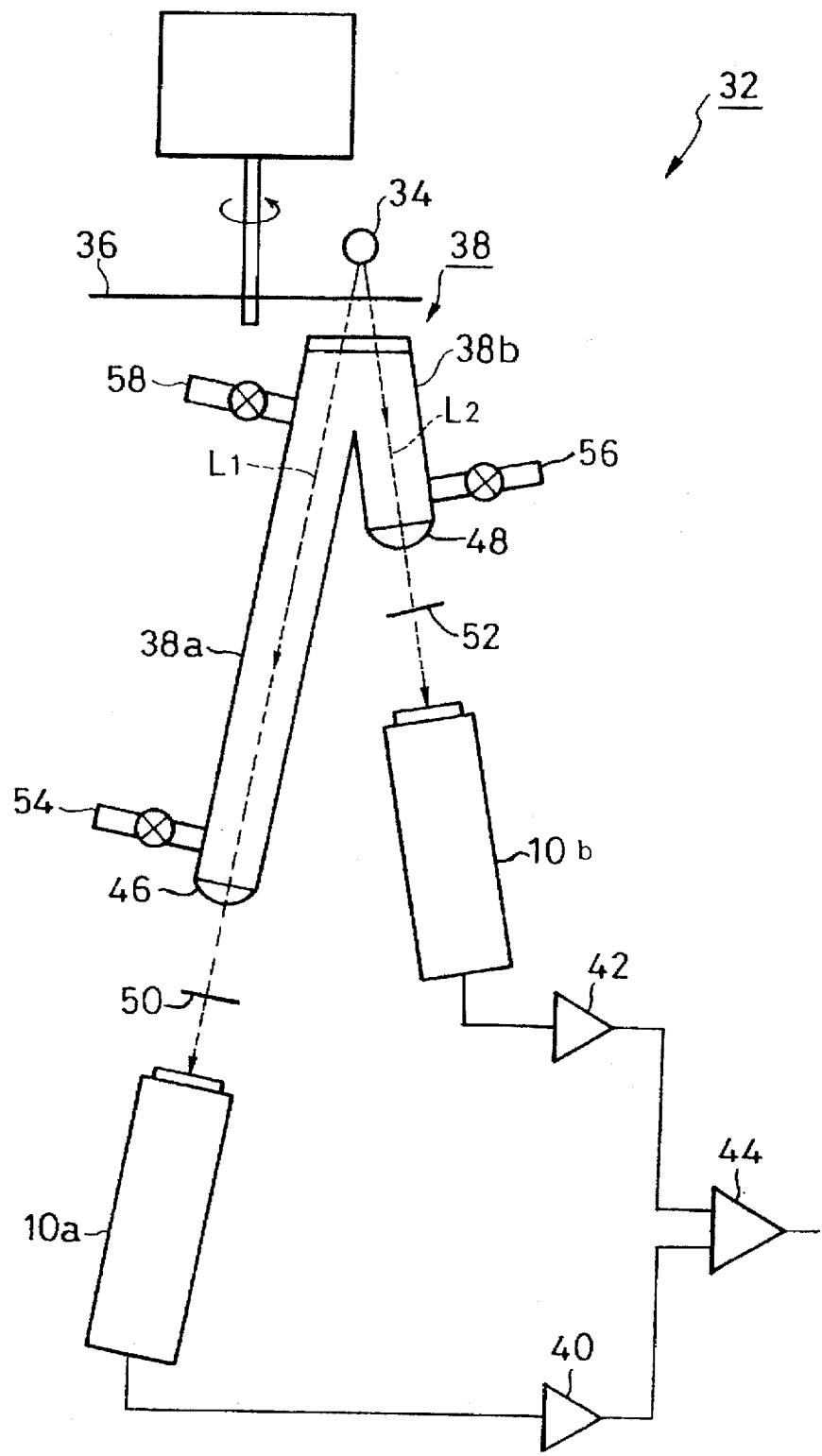
FIG. 2 is an explanatory view showing a configuration of a gas analyzing apparatus in accordance with a first embodiment of the present invention.

FIG. 2 shows a first embodiment of the gas analyzing apparatus in accordance with the present invention.

A gas analyzing apparatus 32 shown in this drawing comprises a light source 34 for emitting an infrared luminous flux, a rotary sector 36 for changing the infrared luminous flux from the light source 34 into intermittent light, a sample cell 38 comprising a first cell portion 38a and a second cell portion 38b, a first detection means 10a composed of the detection means 10 shown in FIG. 1 containing only $^{13}CO_2$ gas, a second detection means 10b containing only $^{12}CO_2$ gas, a first amplifier 40, a second amplifier 42, and an indicator 44.

While the sample cell 38 comprises the first cell portion 38a and the second cell portion 38b, their optical path lengths are selected according to the ingredients to be measured. Namely, the optical path lengths of the first cell portion 38a and the second cell portion 38b correspond to the mixing ratio of $^{12}CO_2$ and $^{13}CO_2$ gases in the exhalation.

In this embodiment, for example, when the mixing ratio of $^{12}CO_2$ and $^{13}CO_2$ in the exhalation is L:1 (L>>1), the first cell portion 38a and the second cell portion 38b are formed such that the ratio of their optical lengths is L:1. Namely, their optical lengths are longer and shorter for $^{13}CO_2$ and $^{12}CO_2$ gases having low and high concentrations, respectively.

Also, the first cell portion 38a of the sample cell 38 has a plane-convex first condenser lens 46 at a portion through which an infrared luminous flux L1 passes, whereas the second cell portion 38b of the sample cell 38 has a plane-convex second condenser lens 48 at a portion through which an infrared luminous flux L2 passes. These first and second condenser lenses 46 and 48 converge the infrared luminous fluxes transmitted through the sample cell 38 onto the first and second detection means 10a and 10b, respectively, while being sufficiently transparent to light.

The gas analyzing apparatus 32 in accordance with this embodiment is schematically configured as mentioned above. Its operation will be explained in the following.

The two infrared luminous fluxes L1 and L2 emitted from the light source 34 are changed into intermittent light by the rotary sector 36. Then, one infrared luminous flux L1 enters the first cell portion 38a of the sample cell 38. The infrared luminous flux L1 entering the first cell portion 38a is transmitted therethrough and converged by the first condenser lens 46 so as to reach the first detection means 10a.

On the other hand, the other infrared luminous flux L2 enters the second cell portion 38b of the ample cell 38. The infrared luminous flux L2 entering the first cell portion 38a is transmitted therethrough and converged by the second condenser lens 48 so as to reach the second detection means 10b.

Here, in response to the concentrations of $^{12}CO_2$ and $^{13}CO_2$ gases in the exhalation introduced into the ample cell 38, the light quantities of the infrared luminous fluxes reaching the first and second detection means 10a and 10b from the light source 34 change.

When the infrared luminous flux L1 transmitted through the first cell portion 38a enters the first detection means 10a, the $^{13}CO_2$ gas contained therein absorbs, from the infrared luminous flux transmitted therethrough, the infrared luminous flux having a wavelength identical to the wavelength inherent in the $^{13}CO_2$ gas. When the $^{13}CO_2$ gas absorbs the infrared luminous flux having a wavelength identical to its inherent wavelength, the temperature within the gas container 14a rises in response to the light quantity thereof, thereby increasing the pressure therewithin. Based on the increase in pressure within the gas container 14a containing the $^{13}CO_2$ gas, the first detection means 10a measures the $^{13}CO_2$ gas concentration in the sample cell 38.

When the infrared luminous flux L2 transmitted through the second cell portion 38b enters the second detection means 10b, the $^{12}CO_2$ gas contained therein absorbs, from the infrared luminous flux transmitted therethrough, the infrared luminous flux having a wavelength identical to the wavelength inherent in the $^{12}CO_2$ gas. When the $^{12}CO_2$ gas absorbs the infrared luminous flux having a wavelength identical to its inherent wavelength, the temperature within the gas container 14a rises in response to the light quantity thereof, thereby increasing the pressure therewithin. Based on the increase in pressure within the gas container 14a containing the $^{12}CO_2$ gas, the second detection means 10b measures the $^{12}CO_2$ gas concentration in the sample cell 38.

Thereafter, signals taken out from the first and second detection means 10a and 10b are respectively amplified by the first and second amplifiers 40 and 42 and then indicated by the indicator 44 as concentration values.

In the gas analyzing apparatus in accordance with this embodiment, since the first detection means 10a contains only the $^{13}CO_2$ gas, it has a sensitivity only to the infrared luminous flux having a wavelength identical to the wavelength inherent in the $^{13}CO_2$ gas. Accordingly, the first detection means 10a measures only the absorption of the $^{13}CO_2$ gas.

Also, since the second detection means 10b contains only the $^{12}CO_2$ gas, it has a sensitivity only to the infrared luminous flux having a wavelength identical to the wavelength inherent in the $^{12}CO_2$ gas. Accordingly, the second detection means 10b measures only the absorption of the $^{12}CO_2$ gas.

While the case where the $^{12}CO_2$ and $^{13}CO_2$ gas concentrations in the exhalation are measured is explained in this embodiment, concentrations of various ingredients in this exhalation can be simultaneously measured. Namely, in the gas analyzing apparatus in accordance with this embodiment, when a third detection means containing only nitrogen gas, as a part of the detection means 10, for example, is attached to the sample cell 38, the $^{12}CO_2$, $^{13}CO_2$, and nitrogen gas concentrations in the sample gas can be simultaneously measured.

In this embodiment, as the common light source 34 is used for the first and second detection means 10a and 10b, error values in the detection means resulting from fluctuation in luminance of the light source 34 coincide with each other. Accordingly, such errors in measurement can be offset against each other, whereby the concentration of the $^{12}CO_2$ and $^{13}CO_2$ gases in the exhalation can be measured correctly.

Also, in this embodiment, as the sample cell is formed with optical path lengths which are longer and shorter for the $^{13}CO_2$ and $^{12}CO_2$ gases having lower and higher concentrations, respectively, the output values of the plurality of detection means have an improved balance, whereby the concentrations of the $^{12}CO_2$ and $^{13}CO_2$ gases in the exhalation can be measured correctly.

Preferably, in this embodiment, a common power source is used for the detection light source 18 for the first and second detection means 10a and 10b. In this case, error values in these detection means resulting from power source noise can coincide with each other. Accordingly, such errors in measurement can be offset against each other, whereby the concentrations of the ingredients to be measured in the sample gas can be measured correctly.

Also, in this embodiment, as the plane-convex condenser lenses 46 and 48 are used in the exit window portions of the sample cell 38, the configuration becomes simple while reducing the cost.

Preferably, in this embodiment, on paths between the sample cell 38 and the first and second detection means 10a and 10b through which the infrared luminous fluxes pass, optical filters 50 and 52 which cut off, from the infrared luminous fluxes transmitted through the sample cell, wavelengths inherent in the gases contained in the other detection means are disposed, respectively. For example, the filters 50 and 52 may be optical filters such as low-pass filter and high-pass filter. Filters 50 and 52 may be gas filters.

In this embodiment, a low-pass filter cutting off the wavelength inherent in the $^{12}CO_2$ gas from the infrared luminous flux L1 transmitted through the first cell portion 38a is used as the filter 50, while a high-pass filter cutting off the wavelength inherent in the $^{13}CO_2$ gas from the infrared luminous flux L2 transmitted through the second cell portion 38b is used as the filter 52.

Also, for example, a gas filter containing only the $^{12}CO_2$ gas may be used as the filter 50, while a gas filter containing only the $^{13}CO_2$ gas may be used as the filter 52.

Accordingly, even when an ingredient other than the ingredients to be measured is mingled into the gas container of the detection means, the error in measurement resulting from the absorption of the infrared luminous flux by the ingredient other than the ingredients to be measured is prevented from occurring, whereby the concentration of only the ingredients to be measured can be correctly measured.

Preferably, in this embodiment, the sample cell 38 comprises a light pipe whose inside is optically polished, whereby the infrared luminous flux from the light source 34 can efficiently be transmitted through the sample cell 38. Accordingly, the first and second detection means 10a and 10b can correctly measure the concentrations of the ingredients to be measured in the sample cell 38.

Preferably, in this embodiment, a thermostat means 49 which can constantly maintain the temperature of the sample gas within the sample cell 38 is provided, whereby the error in measurement due to changes in the outside air temperature and the temperature within the chamber can be prevented from occurring and, accordingly, correct and sable results in measurement can be obtained even when the gas analyzing apparatus 32 is used for a long period of time.

Preferably, in this embodiment, a means which can homogenize the mixed sate of the sample gas within the sample cell 38 is provided, whereby the sample gas is prevented from generating a convection due to changes in the infrared luminous flux from the light source and the outside air temperature and the ingredients are prevented from being unevenly distributed due to their difference in specific gravity and, accordingly, the concentrations of the ingredients to be measured in the sample cell 38 can be correctly measured.

Namely, in this embodiment, inlet portions 54 and 56 for introducing the sample gases into the sample cell 38 and an outlet portion 58 for discharging the sample gases therefrom are provided for the sample cell 38 such that the sample gases within the sample cell 38 are circulated through the inlet portions 54 and 56 and the outlet portion 58.

Figure 3:
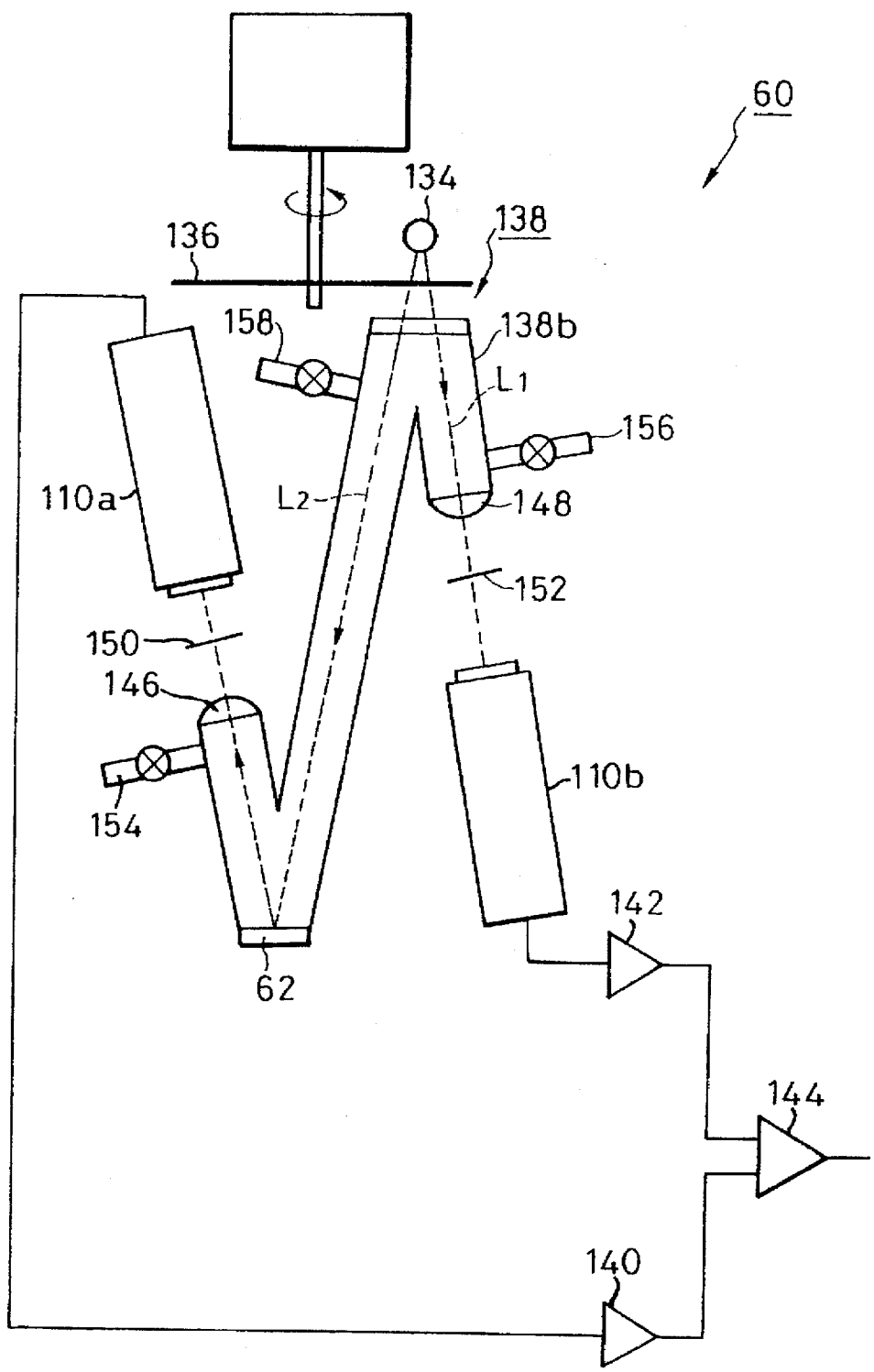
FIG. 3 is an explanatory view showing a configuration of a gas analyzing apparatus in accordance with a second embodiment of the present invention.

FIG. 3 shows a second embodiment of the gas analyzing apparatus in accordance with the present invention.

In this embodiment, parts corresponding to those of the first embodiment are referred to with numerals in which "100" is added to those of the first embodiment, without repeating their explanations.

In a gas analyzing apparatus 60 shown in this drawing, a sample cell 138 is bent at a plurality of portions thereof, while a reflective mirror 62 is disposed at a bent portion of the sample cell 138.

As in the first embodiment, the gas analyzing apparatus 60 in accordance with this embodiment has advantageous effects such as a simple configuration, a high steadiness, and a high selectivity to various measurement ingredients. In addition, as the sample cell 138 is bent, the sample cell 138 can have a small size without shortening its whole optical path length, thereby reducing the size of the gas analyzing apparatus 60.

Figure 4:
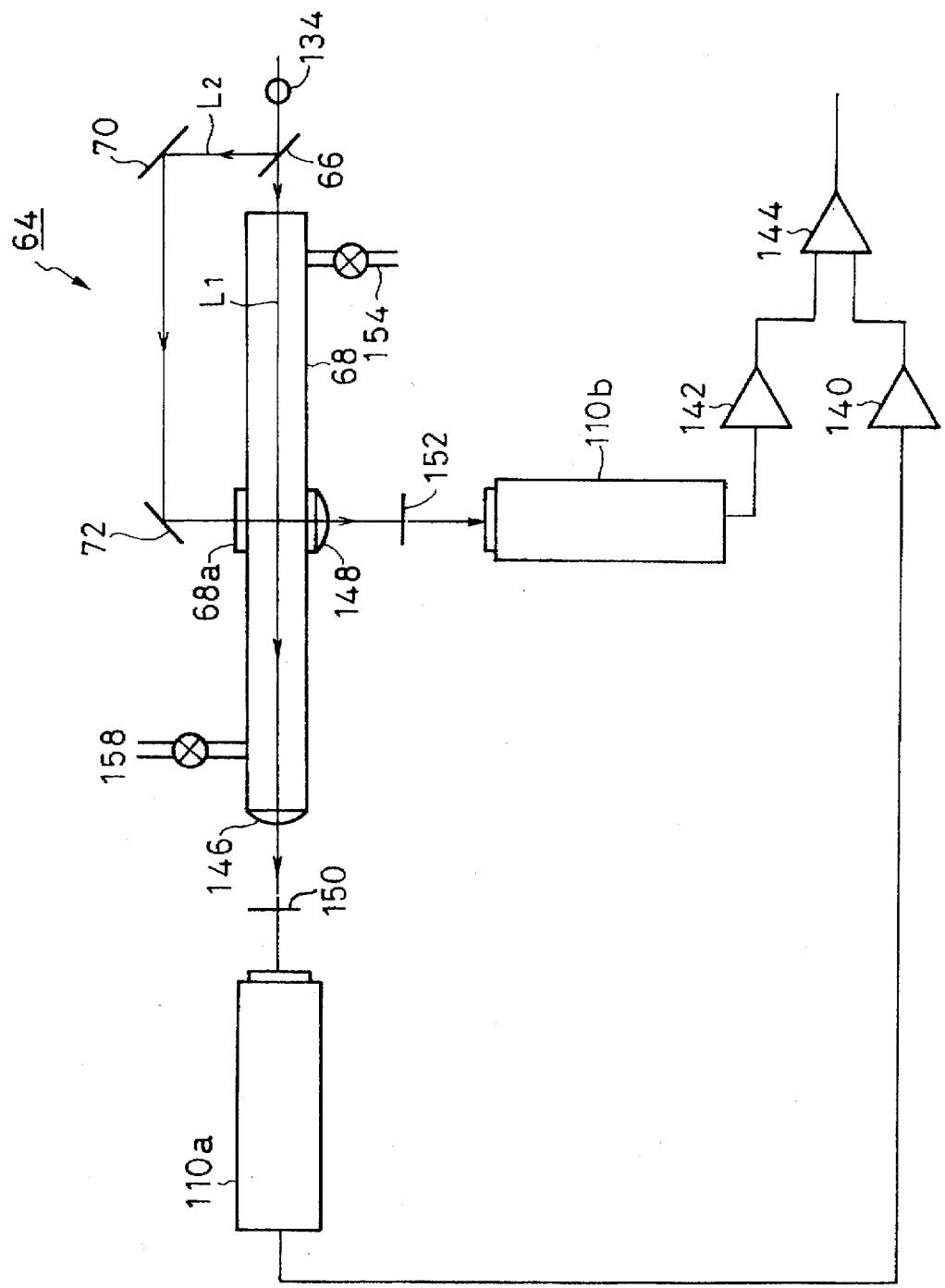
FIG. 4 is an explanatory view showing a configuration of a gas analyzing apparatus in accordance with a third embodiment of the present invention.

FIG. 4 shows a third embodiment of the gas analyzing apparatus in accordance with the present invention.

Here, parts corresponding to those of the first embodiment are referred to with numerals in which "100" is added to those of the first embodiment, without repeating their explanations.

In this embodiment, it is assumed that the influence of $^{13}CO_2$ gas in the air is small. In a gas analyzing apparatus 64 shown in this drawing, a beam splitter 66 is disposed in front of a light source 134 emitting an infrared luminous flux such that one infrared luminous flux L1 of two infrared luminous fluxes divided by the beam splitter 66 is transmitted through a sample cell 68 in its longitudinal direction so as to enter a first detection means 110a.

The other infrared luminous flux L2 of the two infrared luminous fluxes divided by the beam splitter 66 is reflected by reflective mirrors 70 and 72 and then transmitted through the sample cell 68 in its lateral direction from an inlet window portion 68a formed at a side surface thereof, thereby entering a second detection means 110b.

Figure 5:
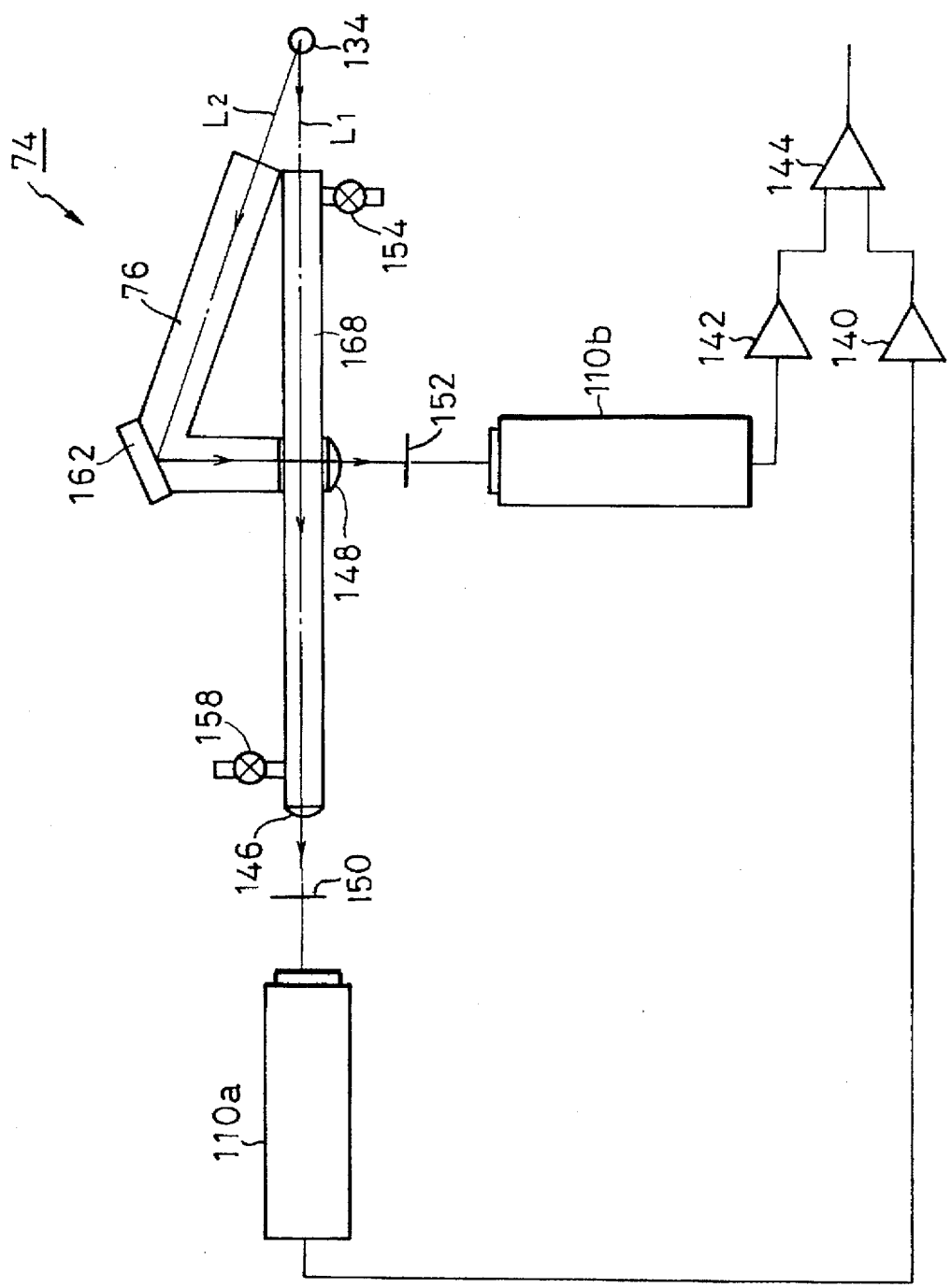
FIG. 5 is an explanatory view showing a configuration of a gas analyzing apparatus in accordance with a fourth embodiment of the present invention.

FIG. 5 shows a fourth embodiment of the gas analyzing apparatus in accordance with the present invention.

Here, parts corresponding to those of the first to third embodiment are referred to with numerals in which "100" is added to those of the first to third embodiment, without repeating their explanations.

In this embodiment, it is assumed that the influence of $^{13}CO_2$ a gas in the air is large. A gas analyzing apparatus 74 shown in this drawing has a sample cell 168 into which an exhalation, namely, a sample gas, is introduced and a cell 76 containing nitrogen gas.

One infrared luminous flux L1 in infrared luminous fluxes emitted from a light source 134 is transmitted through a sample cell 168 in its longitudinal direction so as to enter a first detection means 110a.

The other infrared luminous flux L2 in the infrared luminous fluxes emitted from the light source 134 is transmitted through the cell 76 containing nitrogen gas and the sample cell 168 in their lateral directions and then enters a second detection means 110b.

Here, in order to cancel the errors in measurement resulting from the influence of the nitrogen gas contained in the air with a large amount, the sample cell 168 and the cell 76 are preferably formed with optical path lengths which are substantially optically identical to each other with respect to nitrogen gas.

Thus, as in the first embodiment, the gas analyzing apparatuses in accordance with the third and fourth embodiment have advantageous effects such as a simple configuration, a high steadiness, and a high selectivity to various measurement ingredients. In addition, since the infrared luminous fluxes from the light source can pass through a single sample cell both in its longitudinal and lateral directions, the sample gas can be rapidly introduced into the sample cell and rapidly stabilized in the sample cell.

Figure 6:
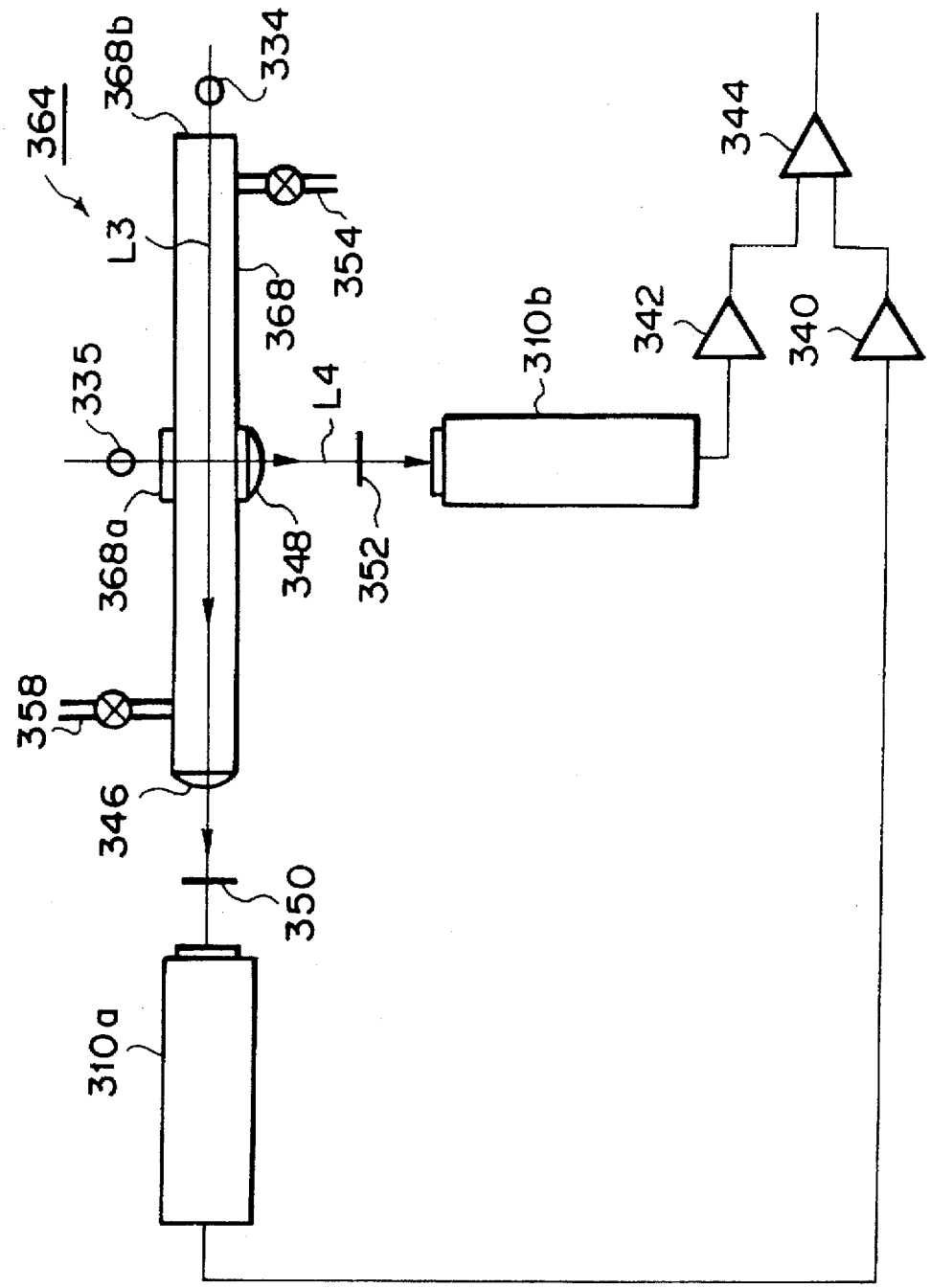
FIG. 6 is an explanatory view showing a configuration of a gas analyzing apparatus in accordance with a fifth embodiment of the present invention.

FIG. 6 shows a fifth embodiment of the gas analyzing apparatus in accordance with the present invention. Here, parts corresponding to those of FIG. 4 are referred to with numerals in which "200" is added to those of the FIG. 4, without repeating their explanations.

In a gas analyzing apparatus 364 shown in this drawing, in addition to a light source 334, a light source 335 similarly emitting an infrared luminous flux is disposed substantially in close proximity to an inlet window portion 368a at a side surface of a sample cell 368.

In the apparatus shown in FIG. 4, in order to divide the infrared luminous flux from the light source 334, for example, a beam splitter has to be disposed between the light source 334 and the sample cell 368.

By contrast, in the fifth embodiment, since the infrared luminous flux from another light source enters the ample cell 368 from its side surface as mentioned above, the beam splitter, for example, becomes unnecessary, whereby the light source 334 can be disposed substantially in close proximity to the sample cell 368.

Namely, an infrared luminous flux L3 from one light source 334, immediately after being emitted therefrom, enters an inlet window portion 368b of the sample cell 368 and then, after being transmitted through the sample cell 368 in its longitudinal direction, is projected onto the first detection means 310a.

On the other hand, an infrared luminous flux L4 from the other light source 335, immediately after being emitted therefrom, enters an inlet window portion 368a of the sample cell 368 and then, after being transmitted though the sample cell 368 in a direction substantially orthogonal to the above-mentioned longitudinal direction, is projected onto the second detection means 310b.

Thus, in this embodiment, without dividing a single infrared luminous flux, the light source 335 is separately disposed near the other inlet window portion 368a, while the light source 334 is placed substantially in close proximity to the inlet window portion 368b. Accordingly, as compared with the foregoing configurations, in the whole optical path through which the infrared luminous flux passes, the length of its portion in the air can be shortened, thereby further reducing the erroneous detection resulting from nitrogen gas in the air.

Here, while the erroneous detection resulting from nitrogen gas in the air can be reduced since the gas analyzing apparatus 364 is constituted as mentioned above, a slight error in measurement may occur due to fluctuations in luminance in the light sources 334 and 335.

However, the error in measurement due to fluctuations in luminance of a plurality of light sources is quite small as compared with that resulting from nitrogen gas in the air. Also, since the former can be reduced, for example, when a common power source is used for the light sources as mentioned above, the gas analyzing apparatus in accordance with this embodiment can further reduce errors in measurement as compared with the foregoing configurations.

What is claimed is:

1. A gas analyzing apparatus comprising a light source emitting an infrared luminous flux; a sample cell which is arranged such that a sample gas is introduced therein and the infrared luminous flux emitted from said light source is transmitted therethrough; and a detection means which contains an absorber and is arranged such that the infrared luminous flux transmitted through said sample cell passes through said absorber and an increase in pressure according to a temperature within an absorber container raised upon absorption of the infrared luminous flux by said absorber is optically detected so as to measure, based on said increase in pressure, a concentration of an ingredient to be measured in said sample gas, wherein, as the absorber contained in said detection means, a gas having an ingredient identical to said ingredient to be measured is used.

2. A gas analyzing apparatus according to claim 1, wherein, in order to measure concentrations of a plurality of ingredients in said sample gas, at least two detection means containing gases having ingredients identical to said plurality of ingredients, respectively, are provided.

3. A gas analyzing apparatus according to claim 2, wherein at least one of said detection means contains a reference ingredient gas and the other detection means contains a gas having an ingredient identical to the ingredient to be measured and said gas analyzing apparatus further comprises a comparator means which compares the concentration value obtained from the detection means containing the gas having an ingredient identical to the ingredient to be measured with the concentration value obtained from the detection means containing a reference ingredient gas.

4. A gas analyzing apparatus according to claim 2, wherein a common power source is provided for detection light sources for said at least two detection means.

5. A gas analyzing apparatus according to claim 2, wherein a common light source is provided for emitting said infrared luminous flux.

6. A gas analyzing apparatus according to claim 2, wherein said sample cell comprises at least two cell portions, said cell portions being formed with with optical path lengths which are increased when concentration of ingredients to be measured is reduced, and which are decreased when concentration of ingredients to be measured is increased.

7. A gas analyzing apparatus according to claim 6, wherein said cell portions being formed with that when the mixing ratio of the ingredients to be measured is A:B, said cell portions are formed such that the ratio of their optical lengths is approximately B:A.

8. A gas analyzing apparatus according to claim 1, further comprising, on a path between said sample cell and detection means through which the infrared luminous flux passes, a gas filter containing a gas having an ingredient identical to the ingredient contained in another detection means.

9. A gas analyzing apparatus according to claim 1, further comprising, on a path between said sample cell and detection means through which the infrared luminous flux passes, an optical filter which cuts off, from the infrared luminous flux transmitted through the sample cell, a wavelength inherent in the gas contained in another detection means.

10. A gas analyzing apparatus according to claim 1, wherein a condenser lens is used in an exit window of said sample cell.

11. A gas analyzing apparatus according to claim 1, wherein said sample cell comprises a light pipe whose inside is optically polished.

12. A gas analyzing apparatus according to claim 1, wherein said sample cell is bent at a plurality of portions thereof and a reflective mirror is disposed at each bent portion of said sample cell.

13. A gas analyzing apparatus according to claim 1, further comprising a thermostat means which can constantly maintain the temperature of the sample gas within said sample cell.

14. A gas analyzing apparatus according to claim 1, further comprising a means which can homogenize a mixed state of the sample gas within said sample cell.

15. A gas analyzing apparatus according to claim 1 wherein the sample cell into which a sample gas is introduced further comprises at least one reflective mirror which is disposed on a path between the light source emitting said infrared luminous flux and said sample cell, through which the infrared luminous flux passes, such that one part of the luminous flux from said light source is transmitted through said sample cell in its longitudinal direction while the other part is transmitted therethrough in its lateral direction so as to enter the detection means corresponding thereto.

16. A gas analyzing apparatus according to claim 1, wherein said sample cell is a single sample cell, said single sample cell is formed such that the infrared luminous fluxes from the light source can pass through a single sample cell both in its longitudinal and lateral directions thereby crossing each other.

17. The gas analyzing apparatus of claim 16 wherein said light source comprises two separate light sources.

* * * * *